United States Patent [19]

Strommen

[11] Patent Number: 4,703,255
[45] Date of Patent: Oct. 27, 1987

[54] PROBE FOR CORROSION TESTING

[76] Inventor: Roe Strommen, Rydningen 23B, Trondheim, Norway, N-7000

[21] Appl. No.: 772,379

[22] Filed: Sep. 4, 1985

[51] Int. Cl.$^4$ ............................................. G01N 27/26
[52] U.S. Cl. ................................ 324/65 CR; 204/1 T
[58] Field of Search ................ 422/53; 204/1 T, 404; 324/347, 348, 332, 333, 71.2, 65 CR, 65 P

[56] References Cited

U.S. PATENT DOCUMENTS 3,209,249  9/1965  Warfield ............................ 324/65 P

FOREIGN PATENT DOCUMENTS 1430214  3/1976  United Kingdom ................ 204/404

Primary Examiner—Reinhard J. Eisenzopf
Assistant Examiner—Jose M. Solis
Attorney, Agent, or Firm—James E. Pittenger

[57] ABSTRACT

A probe for testing for a corrosive environment in a concrete body by measuring the current and the voltage between two metallic elements of different materials, one of which being of a material similar to that of the reinforcement members to be provided in the concrete body. The two elements are rods arranged with holding means to maintain the elements in a parallel relationship when preparing the concrete in situ.

4 Claims, 1 Drawing Figure

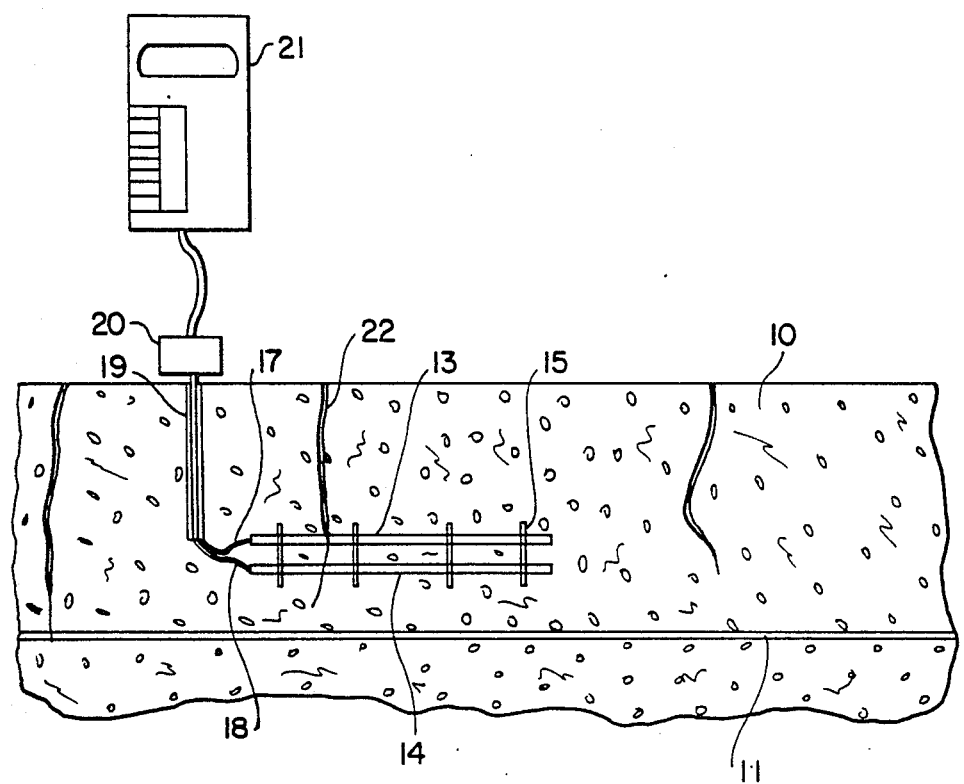

PROBE FOR CORROSION TESTING

This invention relates to a probe of the kind described in the introductory part of claim 1, for corrosion testing, particularly for testing of corrosion of reinforcement steel in concrete.

Reinforcement steel in concrete is generally liable to corrode. It is known to embed probes in the concrete to measure and detect changes in the state of the concrete due to intrusion of water, oxygen, chlorides and other changes influencing the electro-chemical reactions on the probes.

An object of the invention is to provide an improved probe for testing the liability of corrosion in a concrete construction with reinforcement steel. A further object is to provide a probe for permanent monitoring the state of a concrete body in regard of corrosive properties. Still a further object is to provide a probe with two active metallic members, one of which being of a steel similar to that of the reinforcement members.

According to the invention, a novel and improved probe is provided as described in patent claim 1. The electrically active members of this probe are electrically connected to a terminal outside the concrete structure, to be a part of a measurement circuit, to measure the potential between said members and the current flowing between them. Said active members are arranged electrically insulated from the reinforcement members of the concrete structure.

A probe of this kind can be used in concrete structures for quais, bridges, offshore platforms, dams etc.

Further features of the invention are described in the subclaims.

The drawing is a section through a concrete structure provided with an embedded probe according to an embodiment of the invention.

In the drawing is shown a concrete structure 10, which can be a part of a column of a bridge immersed in water or a part of an offshore platform. The concrete structure 10 is provided with a plurality of reinforcement bars in a manner known per se, of which one is illustrated at 11. In this concrete structure are embedded a steel bar 13 and a copper bar 14, both being cylindrical. To keep the bars 13 and 14 in a predetermined distance and fixed mutual arrangement, four holders 15 are provided. Each holder 15 consists of a nonconducting plate with two openings 16, one for each of the rods 13 and 14, with a predetermined distance between the openings. The holders 15 are provided to be introduced on the rods 13 and 14 before their arrangement in the test area prior to the pouring of the unhardened concrete.

The rods 13 and 14 can have a length of 1-2 meter, a diameter of 5-20 mm and a mutual distance of 10-200 mm. The rods can also be made of tubing, provided that the material is suitable for the tests intended.

To connect the rods 13 and 14 electrically to a measurement circuit, each is connected to an electric wire, 17 and 18, respectively. The electric wires 17 and 18 are covered by a tube 19 being of a nonconducting material. At the surface of the concrete structure 10, a terminal unit 20 is arranged. The purpose of the terminal unit 20 is to connect the probe to a measurement circuit 21 illustrated schematically. The measurement circuit, which may be of a suitable known type designed to measure voltage and current, will not be further described.

The measurement unit 21 is provided to measure the voltage potential between the two rods 13 and 14. Due to the difference in material, a potential will exist between said two rods, 13 and 14. This potential is influenced by the environment of the rods 13 and 14, depending on the corrosiveness of this environment. Thus it is possible to register very small changes in the potential and yet be aware of any adverse development in the corrosion, which will represent a threat to the reinforcement material.

Correspondingly, the measurement of the current between the rods 13 and 14 will give information on the electrical resistance of the concrete body between the rods. Any intrusion of clorides in this area will lower the resistance and highten the risk of corrosion. Increase in chloride content and in dilution of the concrete, which can both be registred by an increase in potential between the rods 13 and 14, will create greater corrosion on any reinforcement member embedded.

At 22 is designated a fissure devoloped from the surface of the concrete body to the probe. Through this fissure 22, water and other impairing matter will penetrate into the concrete and change the electro-chemical state.

Alternatively, one or both of the rods 13 and 14 can have a flattened section, e.g. that of a strip.

I claim:

1. Probe for corrosion testing in a concrete structure, comprising a pair of metallic elements of different materials, of which one is of a material similar to that of a reinforcement steel to be embedded in the concrete structure, characterized in that the metallic probe elements are of an elongated shape, the probe further comprising at least two holding means of an electrically nonconducting material, being provided to engage with said elements at different locations along the probe to maintain them in a predetermined mutual distance during the mounting in situ of the probe and the filling with concrete in a nonhardened state.

2. Probe according to claim 1, characterized in that the metallic elements are solid metallic rods, of a length exceeding 500 mm.

3. Probe according to claim 1, characterized in that one other of the probe elements is made of copper.

4. Probe according to claim 1, characterized in that at least one of the probe elements is a plate.

* * * * *